(12) United States Patent
Kelly, Jr. et al.

(10) Patent No.: US 6,475,152 B1
(45) Date of Patent: Nov. 5, 2002

(54) BIOPSY NEEDLE GUIDE FOR ATTACHMENT TO AN ULTRASOUND TRANSDUCER

(75) Inventors: Walter Patrick Kelly, Jr., Dracut, MA (US); Marienne Moro Sanders, Watertown, MA (US); Matthew A Keary, Etna, NY (US); Alec Rooney, North Eliot, ME (US); Benjamin M Herrick, Boxborough, MA (US); Brevard S Garrison, Reading, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/524,466

(22) Filed: Mar. 13, 2000

(51) Int. Cl.⁷ .................................................. A61B 8/00
(52) U.S. Cl. ..................................................... 600/461
(58) Field of Search ............................... 600/439, 459, 600/461, 471

(56) References Cited

U.S. PATENT DOCUMENTS

| | | | |
|---|---|---|---|
| 4,491,137 A | * 1/1985 | Jingu | 600/461 |
| 4,742,829 A | * 5/1988 | Law et al. | 600/461 |
| 4,899,756 A | 2/1990 | Sonek | 128/662.05 |
| 5,052,396 A | * 10/1991 | Wedel et al. | 600/461 |
| 5,076,279 A | 12/1991 | Arenson et al. | 128/662.05 |
| 5,623,931 A | * 4/1997 | Wung et al. | 600/461 |
| 5,924,992 A | * 7/1999 | Park et al. | 600/461 |
| 5,941,889 A | * 8/1999 | Cermak | 606/130 |

* cited by examiner

*Primary Examiner*—Francis J. Jaworski
(74) *Attorney, Agent, or Firm*—John Vodopia

(57) ABSTRACT

A biopsy needle guide in accordance with the invention is configured for attachment to an ultrasound transducer. The biopsy needle guide is arranged in two sections, an inner attachment block and an outer attachment block. The inner attachment block includes (i) a coupler which attaches the inner attachment block to the ultrasound transducer and (ii) a first engagement structure which extends from a surface thereof. The outer attachment block includes a biopsy needle guide through hole and a second engagement structure. The second engagement structure releasably mates with the first engagement structure even when the inner attachment block is covered by a sterile film sheath.

19 Claims, 3 Drawing Sheets

BIOPSY NEEDLE GUIDE FOR ATTACHMENT TO AN ULTRASOUND TRANSDUCER

FIELD OF THE INVENTION

This invention relates to ultrasound transducers and, more particularly, to a biopsy needle guide which is attachable to an ultrasound transducer and is configured such that an outer segment thereof resides exterior to an enclosing film sheath so as to avoid a need for repeated sterilizations of an inner segment thereof and to enable disposal of the outer segment after use.

BACKGROUND OF THE INVENTION

Needle guide adapters for mounting upon ultrasound transducers are known in the prior art. Such needle guides enable arrangement of a biopsy needle with respect to the ultrasound transducer so that, upon insertion of the tip of the needle into a patient, the tip enters a plane that is being imaged by the transducer. U.S. Pat. No. 5,076,279 to Arenson et al. illustrates one such needle guide adapter.

FIG. 1 is illustrative of the configuration of the Arenson et al. biopsy needle guide and illustrates its positioning over an ultrasound transducer 10 which has, in turn, been covered by a sterile film sheath 12. The biopsy needle guide 14 attaches exteriorly to sterile film sheath 12, via interaction of a spring latch 16 with an opposed side of ultrasound transducer 10 and sterile film sheath 12. Biopsy needle guide 14 includes an angled through-hole 18 which is adapted to accept a biopsy needle 20 and to guide its tip 22 to a region within a patient that is being imaged by ultrasound transducer 10. A latching mechanism 24 is actuable to fix biopsy needle 20 in through hole 18.

A problem presented by the Arenson et al. configuration of in FIG. 1 is that it will tend to accumulate blood and other fluids within through hole 18 which renders it difficult to clean and sterilize for re-use. Accordingly, substantial care must be taken during any subsequent sterilization to assure that all such fluids are totally inactivated, or to completely dispose of needle guide 14 after each use. Due to the structural complexity of needle guide 14, this adds a substantial expense to each procedure wherein such a needle guide is employed.

There is therefore a need for a biopsy needle guide that both adapts to coupling to an ultrasound transducer, while exhibiting reduced patient cost per procedure and reduced turn-around time between procedures.

SUMMARY OF THE INVENTION

A biopsy needle guide in accordance with the invention is configured for attachment to an ultrasound transducer. The biopsy needle guide is arranged in two sections, an inner attachment block and an outer attachment block. The inner attachment block includes (i) a coupler which attaches the inner attachment block to the ultrasound transducer and (ii) a first engagement structure which extends from a surface thereof. The outer attachment block includes a biopsy needle guide through hole and a second engagement structure. The second engagement structure releasably mates with the first engagement structure even when the inner attachment block is covered by a sterile film sheath. This enables only the outer attachment block to be replaced after each use, while enabling the inner attachment block and its coupling mechanism to be reused during successive procedures.

The coupler that attaches the inner attachment block to the transducer has a vertical feature on one side and a horizontal feature on the other side. Those features mate with corresponding vertical and horizontal features on the transducer, assuring that the attachment blocks cannot be attached in a wrong orientation.

DETAILED DESCRIPTION OF THE PREFERRED EMBODIMENT

Figure 1:
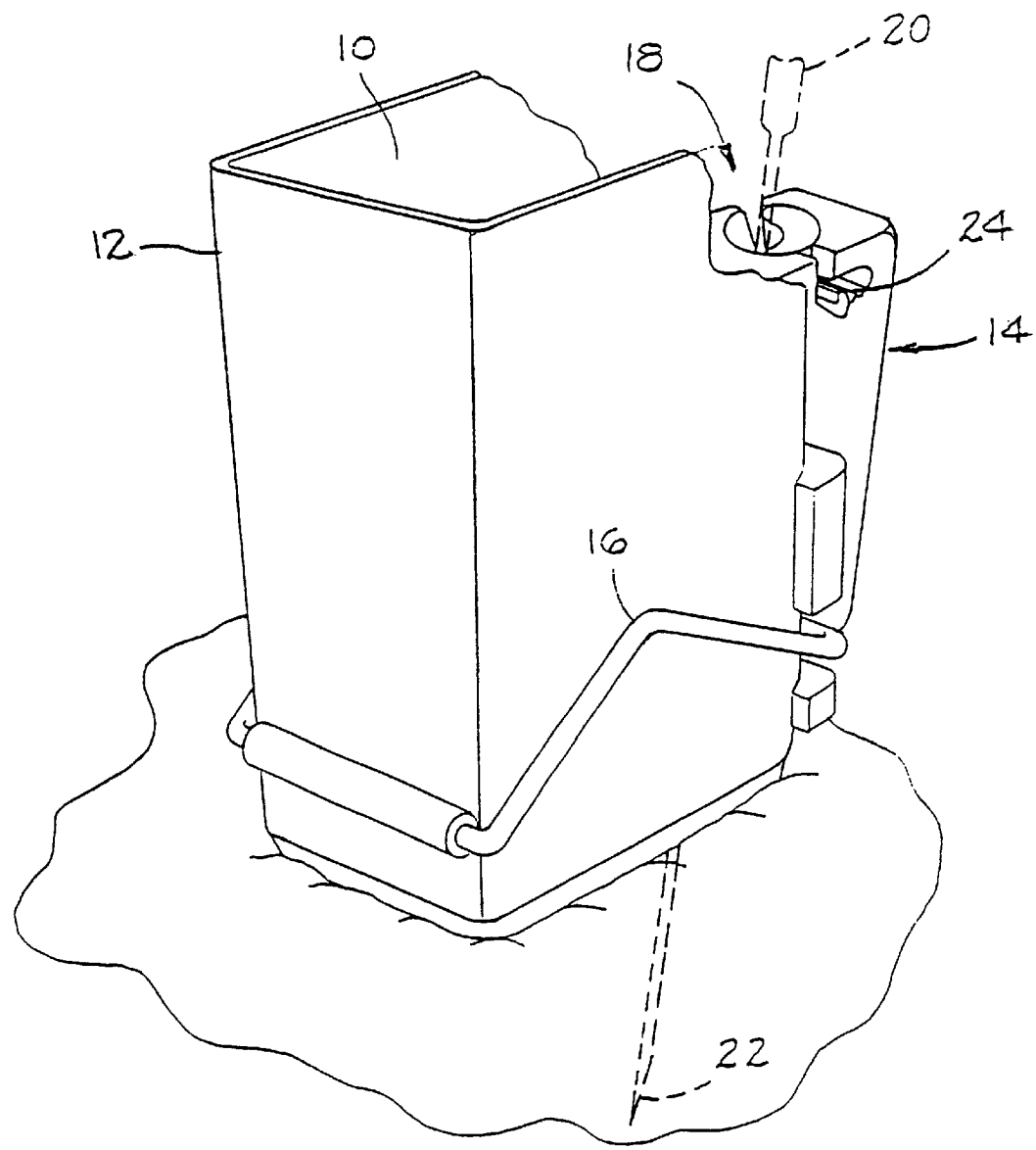
FIG. 1 is a perspective view of a prior art biopsy needle guide and an attached ultrasound transducer head.
Figure 2:
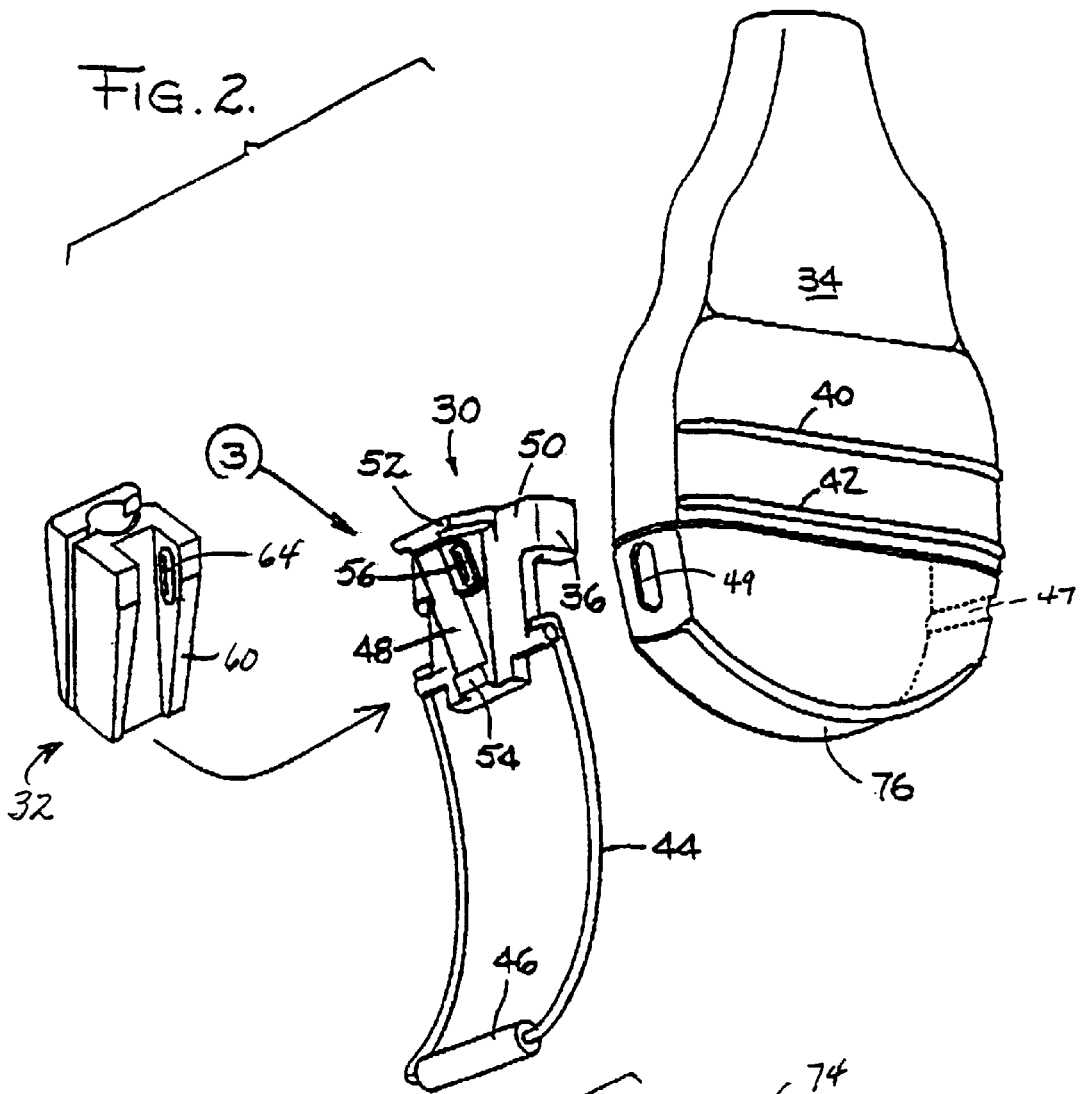
FIG. 2 is an exploded view of a two-part biopsy needle guide in accordance with the invention and an ultrasound transducer to which it couples.
Figure 3:
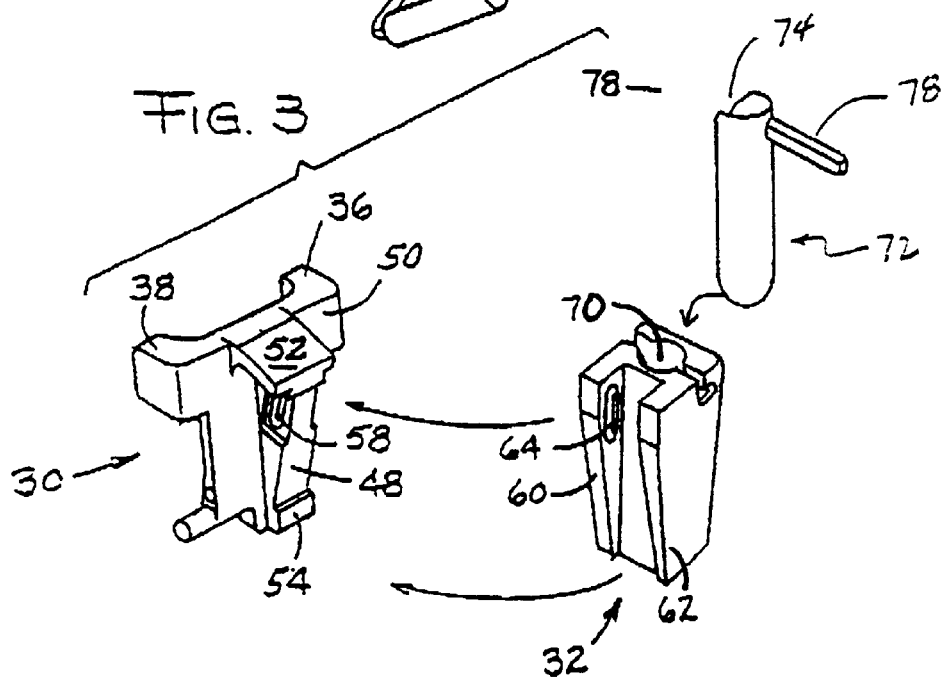
FIG. 3 is an exploded view of an inner attachment block and an outer attachment block of the invention, taken from the perspective of arrow 3 in FIG. 2.

Referring now to FIGS. 2 and 3, a biopsy needle guide incorporating the invention includes an inner attachment block 30 and an outer attachment block 32, both of which couple to an ultrasound transducer head 34. As will be hereafter understood, outer attachment block 32 is adapted to couple to inner attachment block 30 when both inner attachment block 30 and ultrasound transducer head 34 are covered by a sterile film sheath. Accordingly, only outer attachment block 32 needs be replaced after each use, with inner attachment block 30 being usable during successive procedures.

Inner attachment block 30 comprises a pair of arms 36 and 38 that are positional between ridges 40 and 42 on ultrasound transducer head 34. A spring bail 44 is adapted to rotate counterclockwise so as to enable a roller portion 46 thereof to engage a horizontal indentation 47 on the opposed side of ultrasound transducer 34 and to affix inner attachment block 30 thereto. A vertical alignment indentation 49 on an edge of ultrasound transducer 34 is adapted to receive a mating vertical bump (not shown) that extends from between arms 36 and 38 of inner attachment block 30. The arrangements of indentations 47 and 49 assures that the attachment blocks cannot be attached to ultrasound transducer 34 in a wrong orientation. (Note that spring bail 44 and roller 46 are not shown in FIG. 3).

An angled ridge 48 is integral to and extends from an outer surface 50 of inner attachment block 30. The uppermost limit of ridge 48 is defined by a T-shaped extension 52 and its lowermost limit by an outward extension 54. Extensions 52 and 54 act to position outer attachment block 32 when it is brought into an engagement with ridge 48.

On opposed sides of ridge 48 are positioned a pair of indents 56 and 58, with indent 56 being shown in FIG. 2 and indent 58 being shown in FIG. 3. As will be hereafter understood, indents 56 and 58 enable a rigid coupling to be achieved between inner attachment block 30 and outer attachment block 32.

Outer engagement block 32 comprises a pair of walls 60 and 62 which are adapted to sandwich the sides of ridge 48 when outer attachment block 32 is brought into engagement with inner attachment block 30. Inner surfaces of walls 60 and 62 includes fixed lips 64 which are adapted to engage indents 56

The outermost surface of outer engagement block 32 includes a cylindrical opening 70 which is adapted to slidably receive a needle guide pin element 72. Needle guide pin element 72 includes a pathway 74 for receiving a biopsy needle and for guiding the needle tip to a desired imaging region beneath the emitting phase 76 of ultrasound transducer 34. An extension arm 78 enables a user to insert or withdraw needle guide element 72 from guide sleeve 70. Needle guide pin element 72 is turned within block 32 to latch it into a closed position and to captures a needle present therein.

It is preferred that outer engagement block 32 be constructed of a polymer material which enables some flexibility to exist between walls 60 and 62. Such flexibility enables wall 60 to be slightly flexed when outer engagement block 32 is brought into contact with inner engagement block 30, and enables wall 60 to flex outwardly when the innermost edge of lip 64 engages an outer edge of ridge 48.

Figure 4:
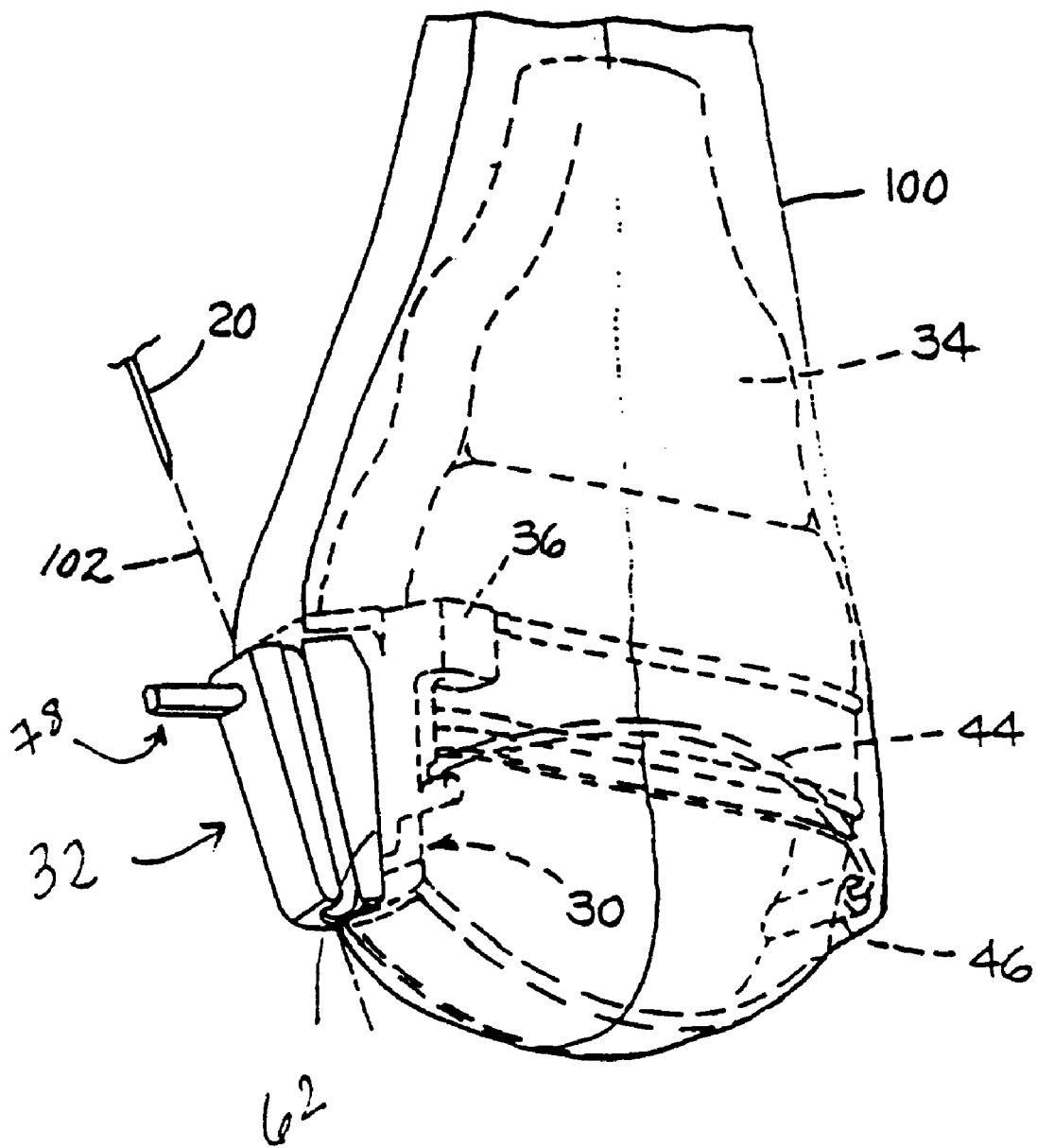
FIG. 4 illustrates a completely assembled outer attachment block, inner attachment block, sterile film sheath and ultrasound transducer head.

Turning to FIG. 4, a fully assembled view is shown of ultrasound transducer 34, inner attachment block 30, outer attachment block 32 with an intervening sterile film sheath 100 that covers both ultrasound transducer 34 and inner attachment block 30. Note that walls 60 and 62 are relatively positioned with respect to each other to accommodate the intervening thicknesses of film sheath 12 on either side of ridge 48 of inner attachment block 30. Also note that extension arm 78 is shown in an alternative configuration, extending perpendicular to ultrasound transducer 34. This, of course, requires a simple modification of block 32.

In operation, inner attachment block 36 is first affixed to transducer head 34 by rotating spring bail 44 so that roller 46 engages an opposite edge of transducer 34. Then, sterile film sheath 12 is placed thereover and outer engagement block 32 is positioned so that walls 60 and 62 sandwich ridge 48. As outer engagement block 32 is pressed into engagement with ridge 48, lip 64 clicks into engagement with indent 56. At this juncture, outer engagement block 32 is fixedly attached to inner attachment block 30 and is ready to receive a biopsy needle 20 along path 102 (shown dashed in FIG. 4).

It is to be noted that the angular configuration of ridge 48 and walls 60 and 62 enable the angular displacement of biopsy needle 102 to be controlled. Accordingly, when ultrasound transducer head 34 is placed on the surface of a patient, and a biopsy needle 102 is threaded through a needle guide 74, the tip of the biopsy needle, as it enters the patient, further enters the imaging region of ultrasound transducer 34, and enables the physician to place the tip of the biopsy needle into a desired anatomically imaged region.

After use, outer attachment block 32 is removed from inner attachment block 30. Thereafter, outward attachment block 32 can be disposed of, leaving inner attachment block 30 for subsequent use.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

For example, the present invention has been described with respect to a biopsy needle, however, those of ordinary skill in the art will recognize the applicability to a variety of instruments. Such other possibilities include a wide variety of exploratory devices, including orthoscopic devices and other invasive devices where it is desirable to monitor such devices with an ultrasonic transducer. Further, while a spring bail 44 has been described as securing (or biasing) the inner attachment block 30 to the ultrasound transducer head 34, other forms of attachment devices are possible, such as an elastic strap, a spring latch, a VELCRO strip (either surrounding the transducer head 34 or mating with strips adhered to the transducer head 34), and a wide variety of other devices.

What is claimed is:

1. A biopsy needle guide for attachment to an ultrasound transducer having an emission face, said biopsy needle guide comprising:
    an inner attachment block, including spring means for coupling to said ultrasound transducer and further including first engagement means extending from a surface thereof; and
    an outer attachment block including (i) means for guiding a biopsy needle tip into an imaging region of said emission face, (ii) second engagement means for releasably mating with said first engagement means, and (iii) coupling means for selectively fixing said first engagement means to said second engagement means upon engagement therebetween so as to fix said outer attachment block to said inner attachment block.

2. The biopsy needle guide as recited in claim 1, wherein said inner attachment block and said outer attachment block are configured so as to be engageable with each other when said inner attachment block is coupled to said ultrasound transducer and said inner attachment block and ultrasound transducer are enclosed by a flexible film sheath.

3. A biopsy needle guide as recited in claim 2, wherein said first engagement means includes a ridge that extends from an outer surface of said inner attachment block and includes plural indents on opposed surfaces thereof.

4. A biopsy needle guide as recited in claim 3, wherein said second engagement means includes a pair of walls that are adapted to sandwich said ridge upon engagement of said first engagement means and said second engagement means, one said wall including a lip adapted to engage at least one of said plural indents.

5. The biopsy needle guide as recited in claim 4, wherein said second engagement means includes a first engagement feature being arranged substantially perpendicular to a plane of the emission face of the transducer, said engagement feature being adapted to engage with a corresponding second engagement feature on said ultrasound transducer.

6. The biopsy needle guide as recited in claim 5, wherein said spring means includes a distal portion that is adapted to mate with a third engagement feature arranged along a longitudinal front face of said ultrasound transducer and to be maintained in place thereby.

7. The biopsy needle as recited in claim 4, wherein said outer engagement block is comprised of a polymeric material that enables said pair of walls to exhibit flexibility upon engagement thereof with said first engagement means.

8. The biopsy needle guide as recited in claim 4, wherein said ridge manifests an outer edge that is angled with respect to said outer surface of said inner attachment block, and supports said outer attachment block in combination with said pair of walls, when said inner attachment block is engaged with said outer attachment block, said means for guiding positioned by said outer edge to orient a biopsy needle tip for subsequent imaging.

9. An instrument guide for attachment to an ultrasound transducer, the instrument guide comprising:
    a first block having first and second opposing surfaces and a securing assembly having at least one movable member configured for engaging the ultrasound transducer, the first surface provided with flanges adapted to mate with an ultrasound transducer; and a second block having a first surface, adapted to mate with the second surface of the first block, and a guide for holding an instrument in alignment with the ultrasound transducer.

10. An instrument guide, as set forth in claim 9, further comprising:

biasing means for biasing the first block to the ultrasound transducer.

11. An instrument guide, as set forth in claim 9, further comprising:

a strap for attaching the first block to the ultrasound transducer.

12. An instrument guide, as set forth in claim 9, further comprising:

a spring bail for attaching the first block to the ultrasound transducer.

13. An instrument guide, as set forth in claim 9, wherein the second surface of the first block has a vertical projection and the first surface of the second block is provided with a vertical groove for receiving the vertical projection.

14. An instrument guide, as set forth in claim 9, wherein the first surface of the first block is provided with a projection adapted to mate with an indent provided on the ultrasound transducer.

15. An ultrasound transducer comprising:

a transducer body containing a transducer;

a first block having first and second opposing surfaces and a securing assembly having at least one movable member configured for engaging the transducer body, the first surface adapted to mate with the transducer body; and a second block having a first surface, adapted to mate with the second surface of the first block, and a guide for holding an instrument in alignment with the transducer body.

16. An ultrasound transducer, as set forth in claim 15, further comprising:

biasing means for biasing the first block to the transducer body.

17. An ultrasound transducer, as set forth in claim 15, wherein the second surface of the first block has a projection being arranged substantially perpendicular to a plane of the emission face of the transducer and the first surface of the second block is provided with a corresponding groove for receiving the projection.

18. An ultrasound transducer, as set forth in claim 15, wherein the transducer body is provided with an indented portion and the first surface of the first block is provided with an projection adapted to mate with the indented portion.

19. An ultrasound transducer, as set forth in claim 15, further comprising a disposable protective sheath adapted to cover the transducer body and the first block while the first block is in engagement with the transducer body while allowing the second block to engage the first block.

\* \* \* \* \*